(12) United States Patent
Lacoste et al.

(10) Patent No.: US 10,533,145 B2
(45) Date of Patent: Jan. 14, 2020

(54) METHOD FOR PRODUCING FATTY ACID ESTERS AND GLYCEROL AT A LOW TEMPERATURE

(71) Applicant: EASYL, Gaillard (FR)

(72) Inventors: François Lacoste, Neuilly sur Seine (FR); Julien Thiel, Arbusigny (FR); Valentin Lair, Chaumont (FR); Samy Halloumi, La Roche sur Foron (FR)

(73) Assignee: EASYL, Gaillard (FR)

( * ) Notice: Subject to any disclaimer, the term of this patent is extended or adjusted under 35 U.S.C. 154(b) by 0 days.

(21) Appl. No.: 16/314,506

(22) PCT Filed: Jun. 30, 2017

(86) PCT No.: PCT/FR2017/051778
§ 371 (c)(1),
(2) Date: Apr. 22, 2019

(87) PCT Pub. No.: WO2018/002559
PCT Pub. Date: Jan. 4, 2018

(65) Prior Publication Data
US 2019/0345413 A1    Nov. 14, 2019

(30) Foreign Application Priority Data

Jul. 1, 2016 (FR) .................................... 16 56335

(51) Int. Cl.
*C11C 3/00* (2006.01)
*B02C 17/20* (2006.01)
(Continued)

(52) U.S. Cl.
CPC .............. *C11C 3/003* (2013.01); *B02C 17/10* (2013.01); *B02C 17/163* (2013.01); *B02C 17/20* (2013.01); *B01J 23/002* (2013.01)

(58) Field of Classification Search
CPC .... C10G 2300/1014; C10G 2300/1018; C10G 3/50; C11C 3/003; B02C 17/10; B02C 17/163; B02C 17/20; B01J 23/002
(Continued)

(56) References Cited

U.S. PATENT DOCUMENTS 3,442,359 A   5/1969  Atchison
5,908,946 A   6/1999  Stern et al.
(Continued)

FOREIGN PATENT DOCUMENTS

EP    0 523 767 A2    1/1993
EP    0 924 185 A1    6/1999
(Continued)

OTHER PUBLICATIONS

International Search Report, dated Oct. 10, 2017, from corresponding PCT/FR2017/051778 application.

*Primary Examiner* — Deborah D Carr
(74) *Attorney, Agent, or Firm* — Young & Thompson

(57) ABSTRACT

A method for producing fatty acid alkyl esters and glycerol implementing a set of transesterification reactions between at least one vegetable or animal oil and at least one aliphatic monoalcohol includes: introducing, into a three-dimensional microball mill at least one vegetable and/or animal oil, at least one aliphatic monoalcohol and at least one heterogenous and/or homogenous catalyst in order to form an initial mixture; grinding the initial mixture at a temperature≤50° C., in a three-dimensional microball mill, for a residence time≤5 minutes; recovering, at the outlet of the three-dimensional mill, a final mixture including at least fatty acid alkyl esters, glycerol, the catalyst and the aliphatic monoalcohol that has not reacted; and separating this final mixture of a first phase including the fatty acid alkyl esters and of a
(Continued)

second phase including the glycerol, the aliphatic monoalcohol that has not reacted and the catalyst.

21 Claims, 3 Drawing Sheets

(51) Int. Cl.
*B02C 17/16* (2006.01)
*B02C 17/10* (2006.01)
*B01J 23/00* (2006.01)

(58) Field of Classification Search
USPC .......................................... 554/167
See application file for complete search history.

(56) References Cited

U.S. PATENT DOCUMENTS

| | | | |
|---|---|---|---|
| 6,147,196 A | 11/2000 | Stern et al. | |
| 6,878,837 B2 | 4/2005 | Bournay et al. | |
| 7,145,026 B2 | 12/2006 | Fleisher | |
| 8,362,288 B2 | 1/2013 | Coupard et al. | |
| 8,580,119 B1* | 11/2013 | Shah | C07C 67/03 210/669 |
| 2007/0260079 A1 | 11/2007 | Fleisher | |
| 2015/0336067 A1* | 11/2015 | Ackermann | C10G 32/02 435/167 |

FOREIGN PATENT DOCUMENTS

| | | |
|---|---|---|
| FR | 1 552 884 A | 8/1967 |
| FR | 2 752 242 A1 | 2/1998 |
| FR | 2 838 433 A1 | 10/2003 |
| FR | 2 962 727 A1 | 1/2012 |
| WO | 2009/029898 A2 | 3/2009 |
| WO | WO-2009029898 A2 * | 3/2009 ......... B01D 17/0208 |

\* cited by examiner a)

b)

c)

METHOD FOR PRODUCING FATTY ACID ESTERS AND GLYCEROL AT A LOW TEMPERATURE

TECHNICAL FIELD TO WHICH THE INVENTION RELATES

The present invention relates in general to the production of fatty acid alkyl esters.

It relates more particularly to a method for production at low temperature, namely less than or equal to 50° C., of esters of fatty acid and of glycerol from a vegetable or animal oil and an aliphatic monoalcohol in a three-dimensional microball mill.

TECHNOLOGICAL BACKGROUND

Fatty acid alkyl esters are currently used in numerous uses, such as diesel fuels, household fuels, ecological solvents, starting compounds for the manufacturing of sulfonates of fatty alcohols, of amides, of dimers of esters, etc.

In particular, one of the major uses of fatty acid alkyl esters relates to the production of biodiesel intended to be incorporated into diesel fuel. Biodiesel is in particular a biofuel of agricultural origin that forms an alternative to the usual fuel of fossil origin.

In a known manner, biodiesel or fatty acid alkyl esters are the product of the transesterification reaction between triglycerides (TG) and a monoalcohol, such as methanol, in the presence of a homogenous or heterogeneous catalyst. A second product, glycerol, is also produced during this reaction. According to the nature of the oil used at the beginning, the glycerol can represent from 10 to 15%, by weight, of the products formed. This glycerol can be reused in various uses, but must first be purified (elimination metals, salts, water).

The transesterification reaction can be represented in the following manner when the starting alcohol is methanol:

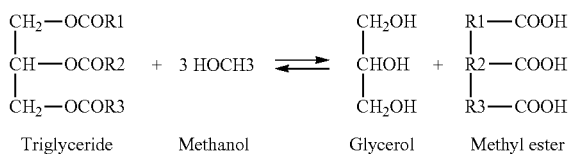

| Triglyceride | Methanol | Glycerol | Methyl ester | wherein R1, R2 and R3 correspond to hydrocarbon chains of fatty acids.

Thus, the molecule of triglyceride is reacted with three molecules of methyl alcohol (or methanol) in order to produce one molecule of glycerol (liquid trialcohol giving fatty acids via transesterification) and three acids called methyl esters (crude biodiesel). Among the sources of triglycerides are vegetable or animal oils and used cooking oils.

Typically, the monoalcohol can be chosen from methanol, ethanol, or butanol; methanol being, however, the most widespread reactive alcohol due to its low price.

Then, the crude biodiesel obtained is refined, then used as a fuel.

For example, in France, according to the decrees from 30 Jun. 2014 and 31 Dec. 2014, fatty acid methyl esters or FAME can be incorporated at most 8% by volume of diesel. The requirements are in particular defined in the standard NF EN 14214:2013. Thus, the biodiesel must contain few diglycerides (maximum concentration of 0.20 mol %), monoglycerides (maximum concentration of 0.20 mol %) and little free glycerol (maximum concentration of 0.02 mol %). Moreover, in order to reinforce the requirements relative to the cold resistance of the diesels based on biodiesel, the concentration of saturated esters must be, by weight with respect to the total weight, less than 30% in the summer and than 16% in the winter. Indeed, the greater the concentration of saturated esters in a fuel, the poorer its cold resistance.

However, the chemical reaction of transesterification described above has two disadvantages: it is slow and in equilibrium, namely when the oil and the alcohol have been transformed into biodiesel and glycerol, the biodiesel and the glycerol can once again be transformed into alcohol and into oil.

This is why, in order to overcome these disadvantages, it is generally considered necessary to use a catalyst and to work under pressure and at a high temperature. Likewise, one way to push the conversion of the oil towards the formation of alkyl (methyl) ester is to work with a large excess of monoalcohol with respect to the stoichiometry and to carry out two reaction steps between which the glycerol produced is eliminated in such a way as to move the equilibrium towards the production of alkyl ester.

Numerous methods for manufacturing fatty acid alkyl esters continuously or discontinuously have already been developed in the prior art.

A first approach involves using the conventional pathways of homogenous catalysis with catalysts soluble in the reaction medium, such as soda or sodium methylate, by reacting a neutral oil and an alcohol (methanol). A representative example of this type of method is the method described in the patent application EP-0.523.767, with continuous implementation of a basic homogenous catalyst.

This type of method, however, has several disadvantages. Once the reaction has ended, the excess of homogenous catalyst present substantially in the glycerine phase in the form of alcoholates and of soaps must be neutralised, then the water and the monoalcohol (methanol) must be eliminated via evaporation. The evaporated monoalcohol (methanol) must often be distilled. For the ester fraction, the traces of alkaline compounds are eliminated by washing with water and drying.

The document U.S. Pat. No. 7,145,026 describes a method for manufacturing fatty acid methyl esters continuously at a temperature ranging from 80 to 180° C. also using a homogenous catalyst. In particular, according to a specific embodiment, this method involves in particular reacting the methanol pre-mixed with a caustic catalyst, such as NaOH, with TGs in a plug flow reactor formed by wound tubes of copper for example of approximately 2 metres (in general ranging from 3 to 9 m for an average diameter of 15 cm) for a residence time ranging from 9 to 16 seconds and a temperature ranging from 50° C. to 87° C. The more the temperature is increased, the greater the rate of conversion into esters: it is for example 78% for a residence time of 9 seconds at 86.8° C. and 43% for a residence time of 9 seconds at 65° C. It is also indicated that the conversion rate is increased by increasing the pressure, for example from 1 bars to 15 bars or the residence time. The increase in temperature and in pressure can be carried out in suitable devices placed upstream of the reactor. In order to obtain fatty acid methyl esters, the products of the reaction (glycerol, catalyst, methyl esters) are separated in a separator provided for this purpose (separation of the products by heating, then the methyl esters are washed with water).

Consequently, even if the conversion rates are relatively high, they remain far from the optimal levels of 90% or more, and this method also has the disadvantage of having to eliminate the catalyst from the reaction products. Moreover, it requires steps of heating and of increasing the pressure that complicate the implementation of this method.

A second approach implements heterogenous catalysts, namely insoluble in the reaction medium.

The document EP 0 924 185 describes in particular a method for manufacturing alkyl esters derived from vegetable oils comprising three steps:
- a first step (a) involves reacting a vegetable oil with an excess of monoalcohol in the presence of a heterogenous catalyst, followed by an elimination of the monoalcohol in excess and a separation of the glycerine, in such a way as to obtain a crude ester containing residual monoglycerides;
- a second step (b), in which the crude ester thus obtained is subjected to a reaction of re-esterification of the residual mono-glycerides into di- and tri-glycerides, in the presence of a heterogenous catalyst; and
- a third step (c), in which an evaporation of the ester at a reduced pressure is carried out with recycling of the evaporation residue into the starting oil of step (a).

The main disadvantage of such a method is the very high economic cost represented by the vacuum distillation of the entire production. Moreover, the presence of recycling also represents an additional cost. Finally, experiments show that even at a highly reduced pressure, the bottom temperature of the column for evaporation of the ester is significant, which leads to a serious risk of degradation of the residue. The latter cannot therefore be totally recycled, it must periodically be purged, which has a negative effect on the yield of the method.

The document FR 2 838 433 also describes a method for producing fatty acid alkyl esters and glycerol in the presence of a heterogeneous catalyst, zinc aluminate. This method involves a succession of three balanced reactions occurring in parallel:
- an oil, such as a colza, palm, sunflower, etc. oil (representing 20 to 80%, preferably 45 to 55% by weight) is reacted with a molecule of monoalcohol, such as methanol, in order to give a molecule of alkyl ester and a diglyceride;
- the diglyceride thus obtained (representing 20 to 80%, preferably 45 to 55% by weight) is reacted with a molecule monoalcohol (methanol) to give a molecule of alkyl (methyl) ester and a monoglyceride;
- the monoglyceride thus obtained is reacted with a molecule of monoalcohol (methanol) to give a molecule of alkyl (methyl) ester and a molecule of glycerine.

The reaction is carried out in general in a plurality of successive fixed-bed reactors operating with an ascending flow and in liquid phase, each of the reactors being supplied with a mixture of colza oil and of monoalcohol (methanol) (first reactor) or for the most part of alkyl (methyl) ester and of monoalcohol (methanol) (second reactor and optionally the following reactors). The reactions are carried out at a temperature ranging from 180° C. to 220° C. at a pressure of 30 bars to 80 bars. Between the reactions, the excess monoalcohol is eliminated by evaporation in order to be recycled and the product obtained is decanted in a settling tank in order to separate the phases rich in alkyl ester from the phase rich in glycerol.

At the reactor outlet, the methyl ester and a joint product of the reaction, glycerol, as well as the excess methanol, are obtained.

Consequently, this method has the disadvantage of being very complicated, of requiring the use of numerous devices positioned successively (reactors/evaporators/condensers/settling tanks, etc.). Moreover, it requires working at high temperatures (180° C. to 220° C.) and at high pressures (30 bars to 80 bars).

The document US 2007/0260079 describes a method for manufacturing biodiesel that can use a homogenous catalyst, a heterogenous catalyst or both.

In particular, the method involves:
- reacting the TGs, the alcohol (methanol), the catalyst in a first reaction zone formed by a mixer followed by a tubular reactor (residence time 20 to 30 seconds at a pressure of 3.5 to 20 bars and a temperature ranging from 70 to 200° C.) in order to form a first intermediate mixture that comprises the product transesterified fatty acid ester, the alcohol that has not reacted, the TGs that have not reacted or have partially reacted;
- eliminating the glycerol and the alcohol that has not reacted from this intermediate mixture in particular via a hydrocyclone that allows to separate the heavier phase, namely the glycerol, from the fatty acid methyl esters formed comprised in a second intermediate mixture;
- bringing this second intermediate mixture to a second reaction zone also comprising a mixer followed by a tubular reactor;
- adding, to this second reaction zone, alcohol and the catalyst (in the mixer) in order to form a third intermediate mixture which, once brought to the reactor (residence time of approximately 30 to 60 seconds at a pressure of 10 to 27.5 bars and a temperature ranging from 70 to 200° C.), allows to form fatty acid alkyl esters and glycerol;
- separating the alcohol, the glycerol and the fatty acid alkyl esters via a hydrocyclone.

Consequently, this method also has the disadvantage of requiring the use of numerous devices (mixer/reactor and hydrocyclone) positioned successively in order to carry out the reaction of transesterification and requiring steps of heating and of pressurising.

The document US 2015/0336067, which describes the manufacturing of biodiesel from a vegetable oil, methanol and a catalyst, is also known from the prior art. These raw materials are placed in a tank that is connected to a vibration device that allowed the reaction of transesterification.

In summary, to manufacture biodiesel, it is currently necessary to use such numerous steps that only large units are in general capable of being economically profitable.

There is therefore a real need for a new method for manufacturing fatty acid alkyl esters that would allow the manufacturing of such compounds simply and economically, for example by having a smaller number of steps, by using less implementation devices (reactor, settling tank, evaporator, condenser, etc. placed successively), while being fast (reduced residence time).

There is also a need to provide a new method in which the manufacturing of these fatty acid alkyl esters does not require any particular heating or pressurising that could increase the manufacturing costs.

The goal of the present invention is consequently to propose a new method for manufacturing fatty acid alkyl esters at least partly avoiding the aforementioned disadvantages.

OBJECT OF THE INVENTION

For this purpose, the object of the present invention is a method for producing fatty acid alkyl esters and glycerol implementing a set of transesterification reactions between at least one vegetable or animal oil and at least one aliphatic monoalcohol comprising the following steps:

(A) the introduction, into a three-dimensional microball mill, separately or in a mixture, of at least one vegetable and/or animal oil, at least one aliphatic monoalcohol and at least one heterogenous and/or homogenous catalyst in order to form an initial mixture;

(B) the grinding of said initial mixture at a temperature less than or equal to 50° C., preferably less than or equal to 25° C., in a three-dimensional microball mill, for a residence time less than or equal to 5 minutes, preferably ranging from 5 to 30 seconds and typically ranging from 5 to 15 seconds;

(C) the recovery, at the outlet of the three-dimensional mill, of a final mixture comprising at least fatty acid alkyl esters, glycerol, the catalyst and an aliphatic monoalcohol that has not reacted; and (D) the separation of this final mixture of a first phase comprising the fatty acid alkyl esters, of a second phase comprising the glycerol and the aliphatic monoalcohol that has not reacted and the catalyst.

For the rest of the description, unless otherwise specified, the indication of an interval of values "from X to Y" or "between X and Y", in the present invention, is understood as including the values X and Y.

According to the invention, a temperature less than or equal to 50° C. includes the following values or any interval between these values: 50; 49; 48; 47; 46; 45; 44; 43; 42; 41; 40; 39; 38; 37; 36; 35; 34; 33; 32; 31; 30; 29; 28; 27; 28; 27; 26; 25; 24; 23; 22; 21; 20; 19; 18; 17; 16; 15; 14; 13; 12; 11; 10; etc.

Also, residence time less than or equal to 5 minutes means a residence time less than or equal to the following values or to any interval between these values: 5 min; 4 min; 3 min; 2 min; 1 min; 50 sec; 45 sec; 40 sec; 35 sec; 30 sec; 25 sec; 20 sec; 15 sec; 10 sec; 8 sec; 5 sec; etc. In general, the residence time of the initial mixture corresponds to the flow rate used during the method over the volume of the initial mixture in this mill (the volume of the initial mixture being equal to the volume of the mill—the volume taken up by the microballs).

Other non-limiting and advantageous features of the method for producing fatty acid alkyl esters according to the invention, taken individually or in any of the combinations technically possible, are described below.

The object of the invention is also a product suitable for being obtained by the aforementioned method, comprising at least fatty acid esters, glycerol, a catalyst and a monoalcohol, characterised in that it comprises less than 30%, by weight, with respect to the total weight of the product, of said monoalcohol.

DETAILED DESCRIPTION OF AN EXAMPLE OF AN EMBODIMENT

The description that will follow in comparison to the appended drawings, given as non-limiting examples, will make it clear what the invention consists of and how it can be carried out.

Figure 1:
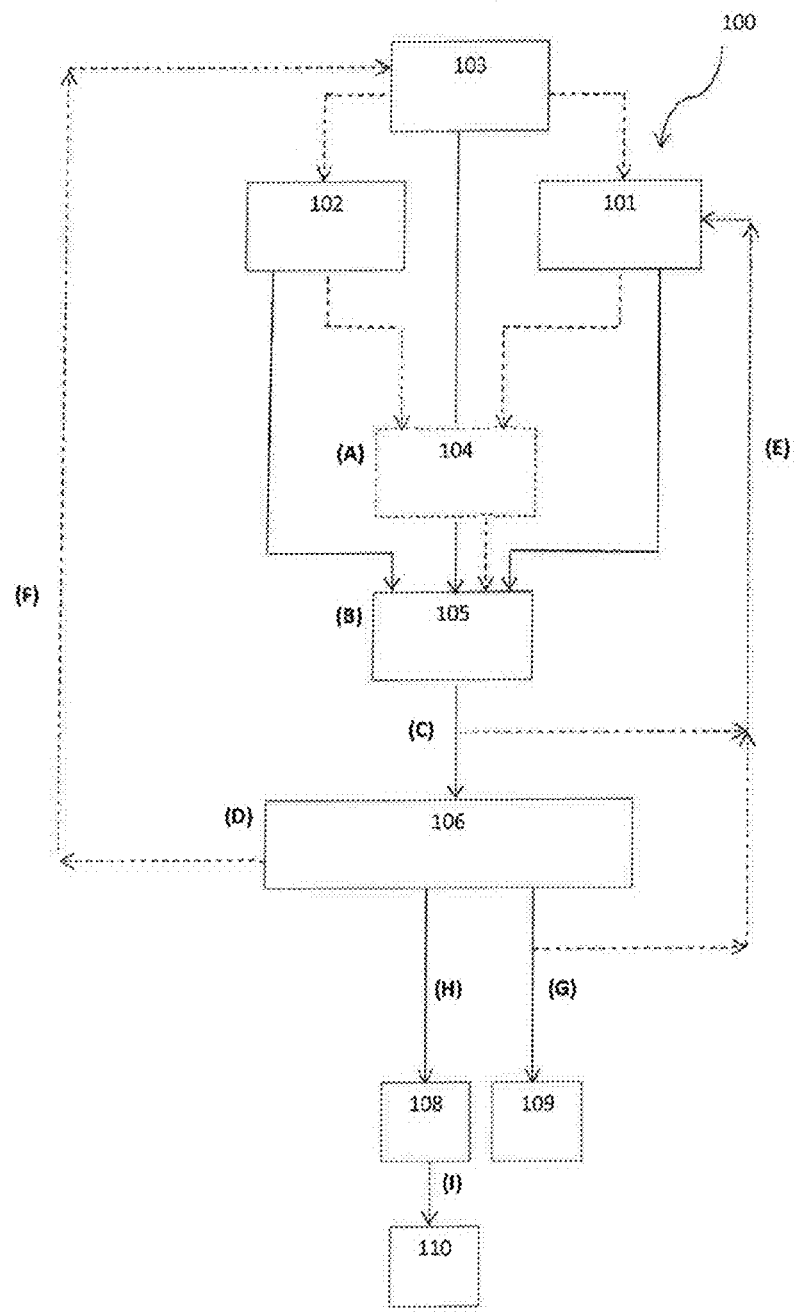
FIG. 1 is a diagram of the various steps of the method according to a specific embodiment of the invention. In this drawing, alternative embodiments of the invention are also shown with dashed lines.

Likewise, table 3 below in the example part is a table of results of the conversion percentages obtained given various oils and while varying the experimental conditions, such as the molar ratio, the mass percent of catalyst, the flow rate of passage, the diameter of the balls; etc.

The Applicant strived to develop a new method for manufacturing fatty acid alkyl esters adapted to an implementation on the industrial scale, which is less costly and simplified with respect to the conventional methods described above.

In particular, the Applicant has discovered surprisingly that the use of a three-dimensional ball mill, usually used in the industry, such as the pharmaceutical industry in order to reduce the size of particles or to carry out homogenous mixtures of two compounds, would allow to carry out an organic chemistry reaction and synthesise fatty acid alkyl esters from a vegetable and/or animal oil and a monoalcohol, with a very high conversion rate, for a single passage, in general greater than or equal to 95%, preferably greater than or equal to 98%.

The facility implemented for carrying out this method is indeed very simple and can be composed only of a three-dimensional microball mill followed by a separator. Moreover, this facility can have a variable size and can be easily installed near the sites for recovery of used oils.

Moreover, as will be demonstrated in the experimental part below, the use of such a mill allows to produce, in a simple and not costly manner, a biodiesel, in a very short time without requiring any particular steps of heating and/or pressurisation. Indeed, the work is generally carried out at ambient temperature and pressure. Moreover, the method of the invention requires preferably a molar ratio "monoalcohol/vegetable and/or animal oil" close to the stoichiometry without it also being necessary to eliminate the monoalcohol during the method or add it in order to move the equilibrium of the transesterification reaction.

Likewise, this method allows to limit the water consumption, in particular when the catalyst used is a homogenous catalyst, with respect to the methods of the prior art.

The method according to the invention also has the advantage of being able to be implemented continuously. These features are important for a use on the industrial scale.

Thus, as mentioned above, the present invention relates to a method for producing fatty acid alkyl esters and glycerol implementing a set of transesterification reactions between at least one vegetable and/or animal oil and at least one aliphatic monoalcohol comprising the following steps:

(A) the introduction, into a three-dimensional microball mill, separately or in a mixture, of at least one vegetable and/or animal oil, at least one aliphatic monoalcohol and at least one heterogenous and/or homogenous catalyst in order to form an initial mixture;

(B) the grinding of said initial mixture at a temperature less than or equal to 50° C., preferably less than or equal to 25° C., in a three-dimensional microball mill, for a residence time less than or equal to 5 minutes, preferably ranging from 5 to 30 seconds and typically ranging from 5 to 15 seconds;

(C) the recovery, at the outlet of the three-dimensional mill, of a final mixture comprising at least fatty acid alkyl esters, glycerol, the catalyst and the aliphatic monoalcohol that has not reacted; and (D) the separation of this final mixture of a first phase comprising the fatty acid alkyl esters and of a second phase comprising the glycerol, the aliphatic monoalcohol that has not reacted and the catalyst.

Preferably, the method further comprises a step (E) of eliminating the monoalcohol before and/or after the step (D) of separation.

In reference to FIG. 1, the method 100 according to the invention will now be described more explicitly below.

First of all, the manufacturing of the fatty acid alkyl esters according to the invention can initially comprise (A) a step of mixing at least one vegetable and/or animal oil with at least one aliphatic monoalcohol, for example via any mechanical means.

For this, the monoalcohol can be stored in a first tank 101, the vegetable and/or animal oil in a second tank 102 and the catalyst in a third tank 103.

According to a specific embodiment, the catalyst can be pre-mixed and placed in suspension with the monoalcohol (for example, when the catalyst used is a homogenous catalyst). It can also be pre-mixed and placed in suspension with the oil (for example, when the catalyst used is a heterogenous catalyst), this pre-mixture being placed in the tank 102.

Wherein the vegetable and/or animal oil optionally containing the catalyst, the monoalcohol optionally containing the catalyst and the catalyst can also be introduced directly into the microball mill 105.

The monoalcohol suitable for the present invention can be for example chosen from all the primary and secondary aliphatic monoalcohols having in general 1 to 8 atoms of carbon. The monoalcohol preferred for the method of transesterification of the present invention is for example chosen from one or more of the following monoalcohols: methanol, ethanol, propanol, isopropyl or butanol; the monoalcohol particularly preferred being methanol or ethanol and is typically methanol.

In particular, methanol is suitable for carrying out the method according to the invention because of its low cost, the fact that it is capable of reacting rapidly and that numerous homogenous catalysts, such as NaOH, dissolve easily therein.

According to the invention, the vegetable and/or animal oil corresponds to natural or created substances, of animal or plant origin, containing for the most part triglycerides (TG), namely at least 50% by weight with respect to the total weight of the oil, preferably at least 60% and typically at least 70%. In particular, the TGs correspond to glycerol, all the hydroxy groups of which are substituted by fatty acids independently having a saturated or unsaturated liner or branched chain, preferably having 4 to 24 atoms of carbon and in particular 12 to 18 atoms of carbon per group of fatty acids.

Preferably, the vegetable and/or animal oil can be any oils known to a person skilled in the art, and can be for example chosen from one or more of the following oils: corn oil, linseed oil, colza oil, olive oil, palm oil, canola oil, copra oil, soybean oil, cottonseed oil, oil of peanut, of jatropha, safflower oil, sunflower oil, copra oil, babassu oil, castor oil, and any oils resulting for example from sunflower or colza via genetic modification or hybridisation or coming from algae, tallow, blubber, the oils of fish, of seal, lard, or a used oil, such as a used frying oil, the fats coming from the treatment of wastewater and even fats from poultry.

It is indeed possible to use used oils, such as oils from frying, from knackery, etc. since the esters manufactured from certain alcohols such as ethyl, isopropyl or butyl alcohol allow to gain over 10° C. in terms of pour point and consequently to use more saturated oils at the start. However, when frying oils, which constitute a very cheap raw material for producing a biodiesel, are used, it is necessary to eliminate, from the reaction mixture, the polymers of fatty acids in order for the mixture of esters to meet the specifications of the standard EN 14214. The goal remains to maintain the acid number of the oil preferably below 0.5 mg KOH/g. Indeed, the presence of fatty acids in the medium can lead to esterification reactions that produce too much water, which can reduce the purity of the glycerine phase jointly produced.

The oils used can also include oils partially modified for example via polymerisation or oligomerisation, such as for example, the "standoils" of linseed oil, of sunflower and the blown vegetable oils. The oils used are neutral or acidic, virgin or recycled.

According to a feature of the invention, it is possible to previously pass (namely before the mixing step (B)), the oil according to the invention through a vacuum dryer in such a way as to obtain a water concentration of less than 700 ppm by weight, also called "dry oil".

The catalyst(s) suitable for the method of the invention can be chosen from a liquid homogenous catalyst and/or a solid heterogenous catalyst.

For example, a homogenous catalyst can correspond to compounds of alkali or alkaline earth metals soluble in the monoalcohol, such as hydroxides and methoxides of the alkali and alkali earth metals and acids, such as $H_2SO_4$.

Preferably, the following homogenous catalysts can be cited: NaOH, LiOH, KOH, $K_2CO_3$, $KNO_3$, KF or $LiNO_3$.

The catalysts according to the invention can be solid heterogenous catalysts, as described by Marinkovich et al in the articles "Calcium oxide as a promising heterogeneous catalyst for biodiesel production: Current state and perspectives" (Renewable and Sustainable Energy Reviews 56 (2016) 1387-1408) and those described in the U.S. Pat. No. 7,145,026.

Preferably, the solid heterogenous catalyst suitable for the method according to the invention is chosen from one or more of the following compounds: calcium oxide, zinc oxide, a mixture of oxide of zinc and of alumina, an aluminate of zinc corresponding to the formula $ZnAl_2O_4$, $(ZnO)_x(Al_2O_3)_y$, where x and y are each between 0 and 2, calcium zincate, calcium diglyceroxide. Preferably, the solid heterogenous catalyst is chosen from: calcium oxide, calcium zincate, calcium diglyceroxide and or one of the mixtures thereof.

In particular, the catalyst according to the invention is the calcium zincate having the formula $Ca[Zn(OH)_3]_2 \cdot 2H_2O$, previously calcined at a temperature ranging from 400° C. to 600° C. In general, the calcination takes place in the presence of air or under an atmosphere of at least one inert gas. Preferably, the calcium zincate has a specific surface area greater than or equal to 10 $m^2/g$.

In particular, the calcium zincate catalyst can be prepared according to the patent application carrying the filing number FR 15 52884 and the catalyst containing zinc oxide can be prepared according to the patent application carrying the publication number FR 2 962 727 or FR 2 752 242.

It should be noted that the catalyst can be a combination of homogenous and heterogeneous catalysts.

In order to carry out step (A) of the method, the monoalcohol, the vegetable and/or animal oil containing the catalyst (as shown according to an embodiment of FIG. 1) are brought, generally without any particular heating step (namely at ambient temperature between 15-25° C.), for example via specific ducts, to a mixer 104 having the function of homogenising the various components in order to form the initial mixture according to the invention. This mixer 104 is well known to a person skilled in the art and will not be described in more detail below. For example, blade mixers can be mentioned.

Alternatively, the preparation of the initial mixture can be carried out previously independently of the method of the invention and introduced as such into the mill 105 or carried out directly in the mill 105.

In general, the catalyst present in the initial mixture represents, by weight, with respect to the total weight of vegetable and/or animal oil less than 4%, preferably from 1 to 4%.

In the sense of the invention, a mass percent of 4% or less includes the following values or any interval between these values: 4; 3.5; 3; 2.5; 2; 1.5; 1; 0.5, etc.

Preferably, the molar ratio "monoalcohol/vegetable and/or animal oil" in the initial mixture is less than or equal to 15, preferably less than or equal to 6 and better less than or equal to 4. Typically, the molar ratio "monoalcohol/vegetable and/or animal oil" in the initial mixture is greater than or equal to 3, the stoichiometric value of the reaction.

In the sense of the invention, a molar ratio less than or equal to 15 includes the following values or any interval between these values: 15; 14; 13; 12; 11; 10; 9; 8; 7; 6; 5; 4; 3.

Likewise, the weight ratio "catalyst/oil+monoalcohol" in the initial mixture is preferably less than or equal to 5%, preferably less than or equal to 3% and typically less than or equal to 2%.

The initial mixture further only comprises water in trace amounts, namely the initial mixture generally has a concentration of water less than or equal to 1500 ppm.

The initial mixture, when it is prepared before its introduction into the mill 105, is brought in a homogenous manner to the three-dimensional microball mill 105 according to the invention in such a way as to proceed to the grinding step (B).

This transport is also preferably carried out without any particular heating, namely at a temperature less than or equal to 50° C., preferably at a temperature less than or equal to 35° C. and typically at a temperature less than or equal to 25° C. It can be carried out for example via ducts provided for this purpose.

In order to better understand the method forming the object of the invention, a three-dimensional microball mill suitable for allowing the production of fatty acid alkyl esters and of glycerol, and thus being part of the invention, will be described below in reference to FIGS. 2 and 3.

Figure 2:
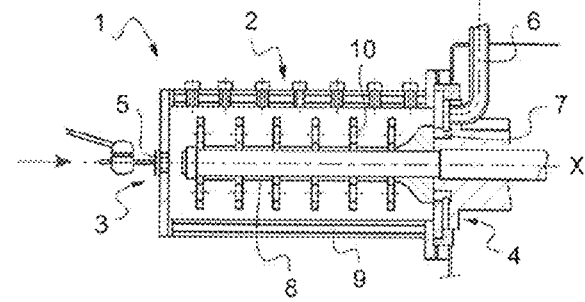
FIG. 2 shows a cross-sectional view along the longitudinal axis XX of a wet-phase three-dimensional microball mill, according to an alternative embodiment suitable for the implementation of the method according to the invention.

As illustrated in FIG. 2, a three-dimensional microball mill 1 comprises at least:
- a stationary grinding chamber 2 having an overall cylindrical shape extending along a longitudinal axis XX, said chamber 2 being filled at least, partly, by said microballs (not shown) and comprises: at a first end 3, at least one inlet 5 used to introduce said initial mixture, and at a second end 4, an outlet 6 comprising a separation means 7 capable of only evacuating the final mixture thus formed (product formed in the mill comprising substantially the fatty acid alkyl esters, the glycerol, the catalyst and the aliphatic monoalcohol that has not reacted) in said chamber 2; and
- a stirrer 8, disposed in the stationary grinding chamber 2, in the form of an elongated rod along the longitudinal axis XX, said stirrer 8 being capable of moving the microball/initial mixture combination.

In particular, the inlet 5 is generally connected to a peristaltic pump (not shown). This pump allows to bring the starting mixture, contained in the mixer 104, into the grinding chamber 2 via the inlet 5. The pump also allows, during the operation of the three-dimensional mill, to bring this initial mixture according to a certain flow rate that is adjustable, hereinafter called "flow rate of passage". This flow rate of passage further forms a current in the grinding chamber 2 allowing to drive the initial mixture from the inlet 5 towards the outlet 6.

The outlet 6 of the grinding chamber 2 comprises in particular the system 7 for separating the microballs from the final mixture. This separation means 7 can be a screen, the orifices of which have a dimension less than that of the microballs, or a separation slot, the width of which is also adapted to retain the microballs in the chamber 2.

The inner wall 9 of the grinding chamber 2 comprises, according to a first embodiment, a smooth inner surface. However, according to an alternative embodiment that will be described below, pins 11 can be arranged on this inner surface 9.

As mentioned above, inside the grinding chamber 2, the stirrer 8, which in addition to the flow rate of passage, also allows the movement of the initial mixture, is disposed.

In particular, the stirrer 8 is capable of turning around the axis X via a rotary shaft (14, FIG. 3) in order to impart, in the grinding chamber 2, an eddy movement onto the initial mixture and thus carry out an intense mixing between this initial mixture and the microballs present in the chamber 2 along the inner wall 9 of this chamber 2.

Figure 3:
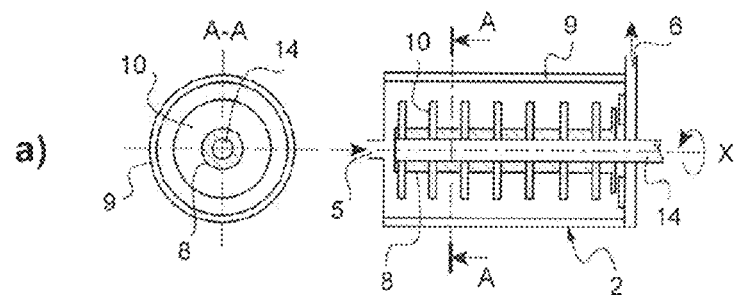
FIG. 3 shows cross-sectional views along the axis XX and the axis AA, of alternative wet-phase three-dimensional microball mills according to FIG. 2 in which: (a) the stirrer is a disc stirrer, (b) the stirrer comprises pins and (c) the grinding chamber is annular.
Figure 3:
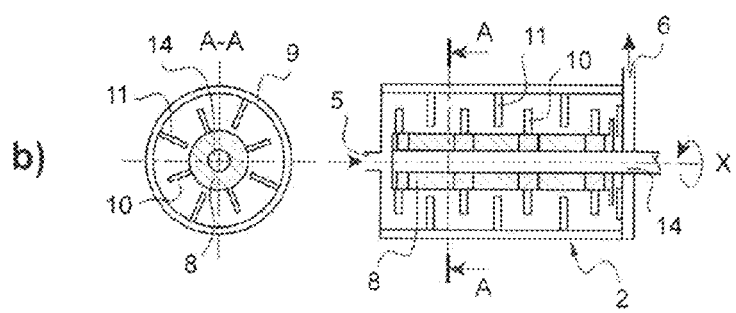
Figure 3:
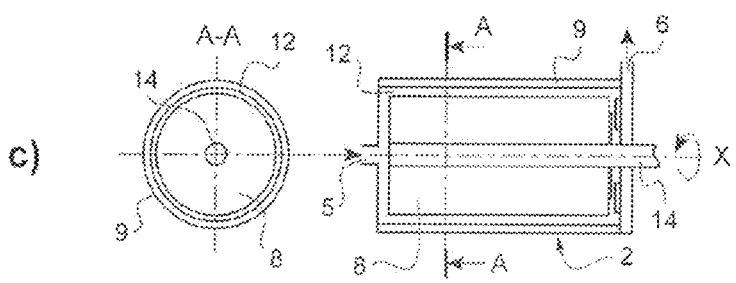

In order to improve this mixing, the stirrer 8, just like the inner wall 9 of the chamber 2, can have various possible configurations shown for example in FIG. 3.

According to a first configuration illustrated in FIG. 3a, the stirrer 8 comprises, along its elongated rod, discs 10, disposed perpendicularly to said rod. Their number can vary from 2 to 8, preferably from 2 to 5. These discs 10 allow on the one hand, to improve the grinding of the starting suspension by better mixing the microballs and on the other hand, to accelerate the reaction time.

According to a second configuration illustrated in FIG. 3b, the stirrer 8 can also comprise, along its rod, one or more perpendicular disposed discs 10 which are further capable of cooperating with pins 11, disposed perpendicularly, with respect to the inner wall 9 of the chamber 2. A pin is in particular in the shape of a ring that extends perpendicularly from the wall 9. For this configuration, the discs 10 and the pins 11 are disposed in staggered rows, namely the discs 10 and the pins 11 are disposed alternatingly in the chamber 2. Moreover, the thickness of the rod 8 is increased with respect to the previous configuration (FIG. 3a) in such a way that the periphery of the discs 10 is close to the inner wall 9 and that of the pins 11 is close to the periphery of the rod of the stirrer 8. Thus, in this configuration, the volume of the chamber is reduced with respect to the previous configuration, thus allowing, better mixing between the initial mixture, the microballs and the inner wall 9 of the chamber 2.

The volume of the chamber 2 can be further reduced as is illustrated in FIG. 3c. In this configuration, the stirrer 8 has an outer diameter slightly less than the inner diameter of the chamber 2, thus forming an annular chamber 12 having a small volume, disposed between the outer wall of the stirrer 8 and the inner wall 9 of the chamber 2. The microballs (not shown) are disposed in this annular chamber 12. During the operation of this configuration, the initial mixture is introduced via the inlet 5 with a certain flow rate, which then passes through the annular chamber 12 until the outlet 6 while being mixed with the microballs.

In general, the mill suitable for carrying out the method according to the invention comprises a grinding chamber having a diameter of 75 mm to 300 mm for a length of 80 mm to 900 mm and a stirrer having a size ranging from 65 mm to 260 mm. Thus, the volume of the grinding chamber varies from 0.35 L to 600 L, preferably from 0.35 L to 62 L.

The geometry of the grinding chamber and of the stirrer can be adjusted by a person skilled in the art according to the desired quantity of fatty acid alkyl esters and of glycerol, as well the desired reaction time. For example, it is also possible for the grinding chamber 2 to comprise an accelerator in order to improve the grinding of the the initial mixture.

Moreover, the microballs housed in the grinding chamber 2 and suitable for the method according to the invention have a substantially spherical shape and have an average diameter ranging from 0.05 mm to 4 mm, preferably from 0.2 to 3 mm, in particular from 0.3 to 2 mm, and typically of approximately 0.5 to 1 mm. Preferably, the diameter of the microballs is less than or equal to 1 mm.

They are preferably chosen from the microballs having a high hardness and resisting abrasion relatively well.

In particular, the microballs have a Vickers hardness measured according to the standard EN ISO 6507-1 greater than or equal to 900HV1, preferably ranging from 900HV1 to 1600HV1, typically ranging from 1000 to 1400HV1.

Advantageously, they have a high true density. In general, the microballs according to the invention have a true density greater than or equal to 2 g/cm$^3$, in particular ranging from 2 to 15 g/cm$^3$, preferably from 3 to 12 g/cm$^3$, and typically from 4 to 10 g/cm$^3$.

Thus, the microballs according to the invention can be microballs made of ceramic, (zirconium oxide $ZrO_2$, made of $ZrSiO_4$ zirconium silicate); microballs made of steel, microballs made of tungsten carbide, microballs made of glass or one of the combinations thereof.

Preferably, the microballs are made of ceramics since they do not generate any pollution by their wear.

In particular, the microballs are made of zirconium oxide.

Optionally, the microballs made of zirconium oxide can be stabilised by another oxide, such as cerium oxide, yttrium oxide and/or silicon.

For example, the following compositions, summarised in table I below, are suitable for forming the microballs according to the invention:

TABLE 1

| Composition of the microballs | Hardness HV1 | True density (g/cm$^3$) | Manufacturer |
|---|---|---|---|
| Microballs made of zirconium oxide stabilised by cerium oxide 80% $ZrO_2$ 20% CeO | 1180 | ≥6.10 | Saint-Gobain (Zirmil ®Y Ceramic Beads) or EIP (Procerox ® ZO Cer) |
| Microballs made of zirconium oxide | 1250 | ≥5.95 | EIP (Procerox ® ZO (Y)) |

TABLE 1-continued

| Composition of the microballs | Hardness HV1 | True density (g/cm$^3$) | Manufacturer |
|---|---|---|---|
| stabilised by yttrium 95% $ZrO_2$ <5% $Al_2O_3$ The rest: $Y_2O_3$ | | | |
| Microballs made of zirconium oxide stabilised by yttrium and silicon: 78% $ZrO_2$, 12% $SiO_2$, 5% $Al_2O_3$ and 4% $Y_2O_3$ | >700 | >4.80 | Saint-Gobain (ER120 Ceramic Beads) |
| Microballs made of $ZrSiCO_4$ zirconium silicate | ≥800 | >6.5 | Saint-Gobain (Rimax Ceramic Beads) |
| Microballs made of glass | 500 | >3.76 | — |
| Microballs made of steel | 700 | >7.7 | — |

In particular, the microballs represent, by volume, with respect to the total volume of the stationary chamber 2, from 50% to 85%, preferably from 55% to 70%.

For example, the wet-phase three-dimensional ball mill suitable for carrying out the method according to the invention can correspond to mills marketed by the companies WAB, Dyno-Mill range: Multi Lab, ECM and KD, Société NETZCH, for example LABSTAR LS1, or Alpine Hosokawa, for example, Agitated Media Mill AHM.

During the grinding step (B), the initial mixture preferably does not undergo a heat treatment. Indeed, the temperature of the initial mixture is less than or equal to 50° C., preferably less than or equal to 35° C. and typically less than or equal to 25° C.

As mentioned above, the residence time of the initial mixture in the mill is very short, and is in general less than 5 min. Thus, the method according to the invention has the advantage of synthesising fatty acid alkyl esters in a very short time, in particular in comparison to the conventional methods of the prior art.

At the outlet of the mill 105, during step (C), the final mixture comprising for the most part fatty acid alkyl esters and a lesser amount of glycerol, an excess of aliphatic monoalcohol (alcohol that has not reacted), as well as the catalyst, is recovered.

In general, this final mixture comprises, by weight, with respect to its total weight:
  60% to 95%, preferably 65% to 92%, and typically 67% to 90% fatty acid alkyl esters
  0% to 30%, preferably 0.5% to 25%, and typically 1% to 20% aliphatic monoalcohol that has not reacted (excess)
  2.5% to 25%, preferably 5% to 20%, and typically 7% to 15%, of a mixture containing glycerol and the catalyst, wherein these two compounds, can or cannot, partially or not, react with each other to form a third compound.

The final mixture can also contain traces of other components, such as partly converted glycerides (monoglycerides, diglycerides and triglycerides), as well as traces of water and of metal ions, in particular alkali ions.

The components that are non-miscible, such as the fatty acid alkyl esters, the glycerol and the catalyst, are then separated during the step (D) that takes place in a separator 106.

Indeed, in this final mixture, the pure glycerol has a density close to 1.2 g·cm$^{-3}$, while that of the fatty acid alkyl esters is around 0.9 g·cm$^{-3}$. In the presence of little methanol, the phase containing for the most part glycerol (G) is thus denser than the ester phase (H) and thus tends to place itself below the latter under the effect of gravity. The ester phase thus forms the supernatant phase when the separation is carried out. In general, the monoalcohol that has not reacted is found, like the catalyst, with the glycerol at the bottom of the separator 106, in the form of a heterogenous viscous phase.

This separator 106 is well known to a person skilled in the art and can correspond to any device capable of separating the upper phase comprising the fatty acid alkyl esters (H) and the lower phase (G) comprising the glycerol that is recovered in a container 109. For example, the separator 106 can be a counter-current settling tank, a centrifugal separator, such as a hydrocyclone, a membrane separator or a settling tank.

This step is also carried out without any particular heating, namely at a temperature less than or equal to 50° C., preferably less than or equal to 35° C. and typically less than or equal to 25° C.

In general, the yield of the transesterification reaction after step (D) is greater than or equal to 95%, better greater than or equal to 98%, and even better greater than or equal to 99%.

Preferably, the method further comprises a step (E) of eliminating the monoalcohol before and/or after the step (D) of separation. The monoalcohol contained in the final mixture at the outlet of the three-dimensional ball mill 105 or at the outlet of the separator 106 (namely located in the glycerol phase) can be recycled. This step of recycling is also well known to a person skilled in the art and can correspond to a step of evaporation/condensation of the monoalcohol as described in the prior art.

Likewise, the catalyst can be recycled during a step (F) according to a technique well known to a person skilled in the art. It can for example undergo one or more washings and or be heat treated before being stored or reintroduced into the process.

Finally, the fatty acid alkyl ester phase (H) coming from the separator 106 can undergo a treatment step (I) in such a way in particular as to meet the specification regarding the concentration of total glycerine (free and bound) of the standard 14214:2013 relative to biodiesel. This treatment (I) can be one or more passages over an ion-exchange resin (108), which can for example be Purolite® PD206, in this case present in order to trap the calcium ion.

This treatment of the crude ester can be carried out in various ways via various devices 110.

For example, the ester can optionally pass through a purification means that eliminates the last traces of insoluble free glycerine (for example by passing through a coalescer), and/or the glycerine dissolved for example on adsorbent masses, such as ion exchange resins, in an adsorber. The treatment of the ester can, in other cases, be carried out via one or more steps of washing the ester with water or simply via filtration.

The present invention can also relate to a product capable of being obtained by the aforementioned method, comprising at least fatty acid esters, glycerol, a catalyst and a monoalcohol, characterised in that it comprises less than 40%, preferably less than 30 mol %, with respect to the total stoichiometry of the product, of said monoalcohol.

Preferably, the monoalcohol, such as methanol, represents, from 0.05 to 20 mol % with respect to the total quantity of product.

The object of the invention is also a product capable of being obtained by the aforementioned method, comprising at least fatty acid esters, glycerol, a catalyst and a monoalcohol, characterised in that it comprises less than 30%, by weight, with respect to the total weight of the product, of said monoalcohol.

Of course, the features described for the method according to the invention as defined above also apply to the present product. They will not therefore be described in more detail below.

EXAMPLES

The description of the trials below is given as a purely informational and non-limiting example. Unless otherwise indicated, the percentages are given by weight.

A° Characterisation: High-Performance Liquid Chromatography HPLC

The HPLC chromatography trials were carried out by using a JASCO chromatograph equipped with a PU-208 quaternary gradient pump, a multi-wavelength detector (MD-2015), a sample changer (AS-2055° and a column oven (co-2065) using a PHENOMENEX LUNA C18 reversed-phase column (250 mm×4.6 mm, 5 μm).

The solvents were filtered through a 0.45 mm filter and degassed with helium. A linear gradient from 100% methanol to 50% methanol+50% 2-propanol-hexane (5:4, v/v) in 35 minutes was used.

The injection volume is 15 mL and the flow rate is 1 mL/min.

The temperature of the column was maintained constant at 40° C.

All the samples were dissolved in the 2-propanol-hexane (5:4, v/v).

Figure 4:
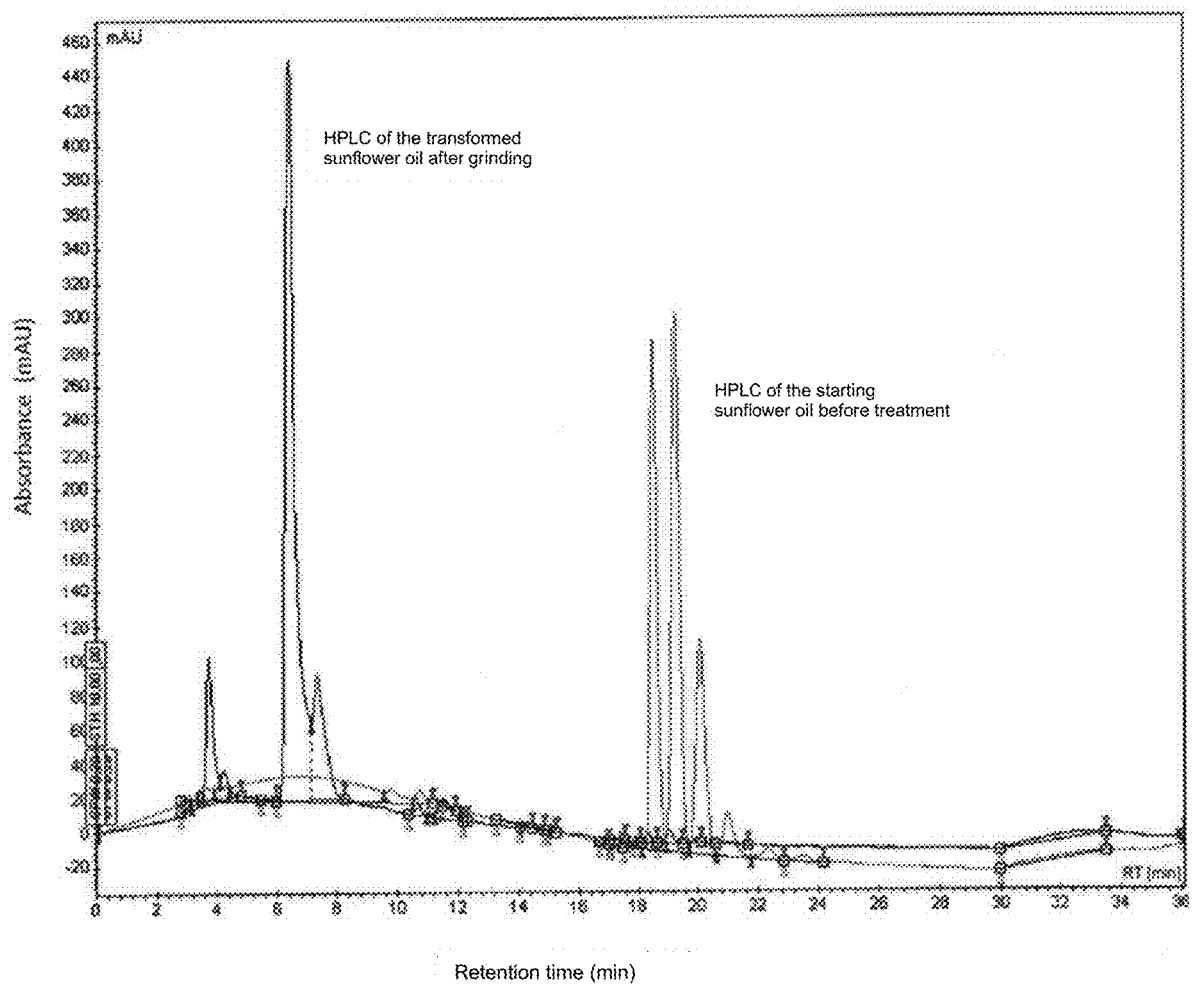
FIG. 4 is a chromatogram resulting from the HPLC analysis of a sunflower vegetable oil before grinding and the HPLC analysis of the transformed sunflower oil after grinding obtained in example n° 3 according to the method of the invention.

The mass percent called FAME (FIG. 4) determined via HPLC is considered to represent the mass yield in % of the fatty acid alkyl esters obtained by the method according to the invention. The peaks of the alkyl esters are identified between 6 and 8 minutes, those of the mono- and or diglycerides between 10 and 15 minutes and finally those of the triglycerides between 18 and 22 minutes. This figure corresponds to the analysis of the reference n° 3 presented in table 3 below.

B° Procedure for Preparing the Tested Samples

✓ Equipment

The trials were implemented in a Dyno Mill MultiLab three-dimensional microball mill from Societe Willy A. Bachofen AG that contains 1 KG of microballs.

The microballs are made of zirconium oxide and have a diameter of 500 μm. They are in particular sold under the brand name Zirmil® Y Ceramic Beads by the company Saint-Gobain.

The grinding chamber of the mill has a capacity of 309 mL and is filled, by volume, with respect to its total volume and according to the trials, with 80% of the microballs described above.

During operation, the microballs are stirred by a stirrer at a speed of rotation of 2890 rpm. The stirrer further comprises two mixer discs made of polyurethane 64 mm in diameter.

✓ Raw Materials
For the trials, the starting raw materials are:

TABLE 2

| Raw materials | Trade name | Reference | Characteristics |
|---|---|---|---|
| *Oil* | | | |
| sunflower oil | Refined sunflower oil | Olvea batch No 12596 | winterised in accordance with the Ph.Eur in force - 55 kg drum |
| soybean oil | Identity-preserved refined soybean oil | Olvea batch No 12280 | compliant with the Ph.Eur in force - 28 kg drum |
| palm oil | Refined palm oil | Olvea batch No 12553 | 10 kg box |
| used oils | Sunflower oil | | Filtered and dehydrated |
| *Catalyst* | | | |
| KOH | Potassium hydroxide 90% | Mon droguiste.com | Packed in 1 kg bag |
| Calcium diglyceroxide | Cadg Calcium diglyceroxide | Easyl SA | Purity > 99% |
| Calcium zincate | ZnO—CaO 99% | Easyl SA | Calcined in air at 400° C. |
| *Monoalcohol* | | | |
| Methanol | 99.9% | Chemical product from PLATRET | |

In particular, the calcium zincate heterogenous catalyst was prepared by following the following method described in particular in the patent FR 15 52884:
  a starting suspension is prepared in a Beaker from calcium hydroxide (74 g) and zinc oxide (162.8 g), in stoichiometric proportions, in demineralised water, or at a concentration of "starting products/demineralised water" of 300 g/L; then, the starting suspension is stirred using a magnetic stirrer;
  it is then brought, via a peristaltic pump having an adjustable flow rate to the Dyno Mill MultiLab mill described above: the flow rates of passage tested in the mill are 30 l/h corresponding to respective residence times of 8 s;
  the starting suspension is then ground in the mill comprising microballs having a diameter of 0.5 mm for a certain time (which depends as indicated above on the flow rate of passage of the starting suspension) at ambient temperature (20-25° C.), thus allowing, at the outlet of the mill, to obtain a suspension of crystals of calcium zincate;
  finally, the suspension of crystals of calcium zincate is recovered and calcined at 400° C. for 60 min ✓ Overall Procedure Implemented for the Trials:
In order to carry out each trial below, the following steps are carried out:
  the catalyst was pre-mixed with the methanol when the latter was homogenous (KOH) or with the oil when it was heterogeneous (calcium zincate, calcium diglyceroxide);
  the oil, the catalyst and the methanol are then mixed in a mechanical paddle mixer for 1 min at ambient temperature (~20-25° C.) in such a way as to obtain an initial mixture;
  once homogenised, this initial mixture was introduced into the mill described above at ambient temperature (20-25° C.) according to the parameters indicated in table 3 below, in such a way as to obtain a final mixture (one passage);
  this final mixture was then decanted in a separatory funnel for 24 hours at ambient temperature (20-25° C.);
  the samples obtained were then analysed by HPLC, in such a way in particular as to determine the mass % of FAME conversion.

C° Results

As table 3 below shows, the method according to the invention allows to obtain excellent conversion rates into fatty acid methyl esters (% FAME conversion rate greater than or equal to 95%) while being easy to implement, while being fast (residence time less than 5 min in the mill) and not requiring steps of heating or of any particular pressurising.

TABLE 3

| | Starting products | | Quantities | | | | | | Parameters of the method | | | | | Results |
|---|---|---|---|---|---|---|---|---|---|---|---|---|---|---|
| Trial | Type of oil | Catalyst | $m_{Methanol}$ (g) | $m_{oil}$ (g) | $n_{metOH}$ (mole) | $n_{oil}$ (mole) | True molar ratio | $m_{catalyst}$ (g) | Mass % Catalyst | Type and diameter of the balls | Rotation (rpm) | Measured flow rate (l/H) | Inlet T (°C.) | Outlet T (°C.) | FAME mass % |
| 1 | Sunflower | calcium zincate | 240 | 1660 | 7.50 | 1.87 | 4.00 | 66.4 | 3.5% | Zirmill 0.5 mm | 2986 | 46.2 | 22 | 30 | 99.5 |
| 2 | Sunflower | calcium zincate | 120 | 830 | 3.75 | 0.94 | 4.00 | 16.6 | 1.7% | Zirmill 0.5 mm | 2986 | 45.6 | 20 | 22 | 88.4 |
| 3 | Sunflower | calcium zincate | 120 | 830 | 3.75 | 0.94 | 4.00 | 16.6 | 1.7% | Zirmill 0.5 mm | 2986 | 68 | 20 | 20 | 94.5 |
| 4 | Sunflower | KOH | 127.987 | 708.8 | 4.00 | 0.80 | 5.00 | 3.5 | 0.4% | Zirmill 0.5 mm | 2986 | 45.8 | 20 | 22 | 95.5 |
| 5 | Soybean | calcium zincate | 120 | 830 | 3.75 | 0.94 | 4.00 | 33.2 | 3.5% | Zirmill 0.5 mm | 2986 | 42.3 | 20 | 22 | 98 |
| 6 | Palm | calcium zincate | 120 | 830 | 3.75 | 0.94 | 4.00 | 33.2 | 3.6% | Zirmill 0.5 mm | 2986 | 45.1 | 36 | 38 | 96 |
| 7 | Used oils | calcium zincate | 120 | 830 | 3.75 | 0.94 | 4.00 | 16.6 | 1.7% | Zirmill 0.5 mm | 2986 | 44.9 | 20 | 22 | 87.6 |
| 8 | Sunflower | calcium diglyceroxide | 120 | 830 | 3.75 | 0.94 | 4.00 | 25.0 | 2.6% | Zirmill 0.5 mm | 2986 | 45.2 | 20 | 24 | 94.8 |

TABLE 3-continued

| | Starting products | | Quantities | | | | | | Parameters of the method | | | | | Results |
|---|---|---|---|---|---|---|---|---|---|---|---|---|---|---|
| | | | | | | True | Mass % | | Type and diameter | Ro- | Measur- ed flow | Inlet | Outlet | FAME |
| Trial | Type of oil | Catalyst | $m_{Methanol}$ (g) | $m_{oil}$ (g) | $n_{metOH}$ (mole) | $n_{oil}$ (mole) | molar ratio | $m_{catalyst}$ (g) | Cata- lyst | of the balls | tation (rpm) | rate (l/H) | T (° C.) | T (° C.) | mass % |
| 9 | Sun- flower | calcium diglycer- oxide | 122 | 830 | 3.81 | 0.94 | 4.07 | 34.0 | 3.6% | Zirmill 0.5 mm | 2986 | 45.2 | 20 | 22 | 97.6 |
| 10 | Sun- flower | calcium zincate | 320 | 922 | 10.00 | 1.03 | 9.66 | 38.0 | 3.1% | Zirmill 0.5 mm | 2986 | 10.9 | 18 | 20 | 98.5 |

The invention claimed is:

1. A method for producing fatty acid alkyl esters and glycerol implementing a set of transesterification reactions between at least one vegetable or animal oil and at least one aliphatic monoalcohol comprising the following steps:
   (A) the introduction, into a three-dimensional microball mill, separately or in a mixture, of at least one vegetable and/or animal oil, at least one aliphatic monoalcohol and at least one heterogenous and/or homogenous catalyst in order to form an initial mixture;
   (B) the grinding of said initial mixture at a temperature less than or equal to 50° C., in a three-dimensional microball mill, for a residence time less than or equal to 5 minutes;
   (C) the recovery, at the outlet of the three-dimensional mill, of a final mixture comprising at least fatty acid alkyl esters, glycerol, the catalyst and an aliphatic monoalcohol that has not reacted; and
   (D) the separation of this final mixture of a first phase comprising the fatty acid alkyl esters and of a second phase comprising the glycerol, the aliphatic monoalcohol that has not reacted and the catalyst.

2. The method according to claim 1, wherein the temperature is less than or equal to 25° C. at step (B).

3. The method according to claim 1, wherein the residence time is ranging from 5 to 30 seconds at step (B).

4. The method according to claim 1, wherein the residence time is ranging from 5 to 15 seconds at step (B).

5. The method according to claim 1, further comprising a step (E) of eliminating the monoalcohol before and/or after the step (D) of separation.

6. The method according to claim 1, wherein the molar ratio monoalcohol/oil in the initial mixture is less than 15 without ever being less than 3.

7. The method according to claim 6, wherein the molar ratio monoalcohol/oil in the initial mixture is less than 6 without ever being less than 3.

8. The method according to claim 6, wherein the molar ratio monoalcohol/oil in the initial mixture is less than or equal to 4, without ever being less than 3.

9. The method according to claim 1, wherein the weight ratio catalyst/oil+monoalcohol in the initial mixture is less than 5%.

10. The method according to claim 9, wherein the weight ratio catalyst/oil+monoalcohol in the initial mixture is less than 3%.

11. The method according to claim 1, wherein the initial mixture has a concentration of water of less than 1500 ppm.

12. The method according to claim 1, wherein the aliphatic monoalcohol is chosen from one or more of the following monoalcohols: methanol, ethanol, propanol, iso-propyl or butanol.

13. The method according to claim 12, wherein the aliphatic monoalcohol is chosen from methanol or ethanol.

14. The method according to claim 1, wherein the catalyst is a solid heterogenous catalyst or a liquid homogenous catalyst.

15. The method according to claim 14, wherein the solid heterogenous catalyst is chosen from one or more of the following compounds: calcium oxide, zinc oxide, a mixture of oxide of zinc and of alumina, an aluminate of zinc corresponding to the formula $ZnAl_2O_4$, $(ZnO)_x (Al_2O_3)_y$ where x and y are each between 0 and 2, calcium zincate and calcium diglyceroxide.

16. The method according to claim 15, wherein the solid heterogenous catalyst is calcium zincate having the formula $Ca[Zn(OH)_3]_2 \cdot 2H_2O$, previously calcined at a temperature ranging from 400° C. to 600° C.

17. The method according to claim 14, wherein the homogenous catalyst is chosen from the hydroxides and methoxides of the alkali and alkali earth metals and acids.

18. The method according to claim 1, further comprising a step of recovering and recycling the catalyst in the method.

19. The method according to claim 1, wherein the yield of the transesterification reaction after step (D) is greater than or equal to 95%.

20. The method according to claim 1, wherein the three-dimensional microball mill comprises at least:
   a stationary grinding chamber having an overall cylindrical shape extending along a longitudinal axis XX, said chamber being filled at least, partly, by said microballs and comprises: at a first end, at least one inlet used to introduce said starting suspension, and at a second end, an outlet comprising a separation means capable of only evacuating the final mixture thus formed in said chamber; and
   a stirrer, disposed in the stationary grinding chamber, in the form of an elongated rod along the longitudinal axis XX, said stirrer being capable of moving the microball/starting suspension combination.

21. The method according to claim 20, wherein the microballs represent, by volume, with respect to the total volume of the stationary chamber, from 50% to 85%.

* * * * *